US00PP14257P29

(12) United States Plant Patent
Hanes

(10) Patent No.: US PP14,257 P2
(45) Date of Patent: Oct. 28, 2003

(54) PETUNIA PLANT NAMED 'WHIP WHITE'

(50) Latin Name: *Petunia hybrida*
Varietal Denomination: 'Whip White'

(75) Inventor: Mitchell Eugene Hanes, Morgan Hill, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/389,098

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by white colored flowers, compact habit and good basal branching.

1 Drawing Sheet

Genus and species: *Petunia hybrida.*
Variety denomination: 'Whip White'.

BACKGROUND OF THE NEW PLANT

The present invention comprises a new and distinct cultivar of petunia, botanically known as *Petunia hybrida,* and hereinafter referred to by the cultivar name 'Whip White'. The new cultivar is asexually reproduced from vegetative cuttings and tissue culture resulting from the cross of the seed/pod parent 99-296-3, a light yellow proprietary line that is unnamed and unpatented ×99-264-4, a purple with a yellow throat proprietary line that is unnamed and unpatented.

'Whip White' is a product of a planned breeding program intended to create new petunia plants with white colored flowers, compact habit, good basal branching and moderately vigorous growth.

The new cultivar was created in 1999 in Gilroy, Calif., and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Whip White'. The data, which defines these characteristics, were collected from asexual reproductions carried out in Gilroy, Calif. The plant history was taken on 6 month old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms: Approximately 5–10 cm.
Width: Approximately 55–70 cm including flowers.
Time to produce a finished flowering plant: 9–11 weeks.
Outdoor plant performance: Full sun, free-flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 3.2–3.7 cm.
Width: 2.3–2.9 cm.
Leaf blade shape: Ovate.
Leaf margin: Entire.
Apex aspect: Obtuse to Acute.
Base aspect: Acuminate.
Leaf color: RHS 137A/B (green); underside: RHS 137C.
Texture: Sparse glandular hairs of various sizes.
Venation: Palmate.
Venation color: RHS 144B (yellow-green).
Petiole length: 0.2–0.3 cm.
Petiole width: 0.2 cm.
Petiole color: RHS 144B (yellow-green).
Petiole texture: Glandular hairs of various sizes.

THE STEM

Length: 40–50 cm.
Diameter: 0.3–0.35 cm.
Internode length: 2.0–2.5 cm.
Color: RHS 144A/B (yellow-green).
Texture: Sparse glandular hairs.
Stem anthocyanin: None.
Peduncle color: RHS 144A/B (yellow-green).
Peduncle length: 2.7–4.0 cm.
Peduncle diameter: 0.1–0.15 cm.
Peduncle texture: Many glandular hairs of various sizes.

THE BUD

Shape: Oblong.
Diameter: 0.4–0.45 cm.
Length: 1.6–2.7 cm.
Color at tight bud: RHS 144C (yellow-green).

THE FLOWER

Blooming habit: Continuous all through the growing season. Good floriferousness.
Inflorescence type: Flowers solitary in upper leaf axis.
Young flower color: RHS N155B (white), but more pure white base color; RHS 144C (yellow-green) mid-veins; RHS 147D (yellow-green) secondary veins fading from corolla.
Young flower floret diameter: 3.7–3.9 cm.
Mature flower color: Front side, RHS N155B (white) but more pure white, bases color; RHS 144C (yellow-green) mid-veins; RHS 147D (yellow-green) minor veins from corolla fading into petals flower color. Underside, RHS N155B (white) but more pure white base color; RHS N144A (yellow-green) mid-veins; RHS 145D (yellow-green) secondary veins.
Corolla tube length: 2.2–2.5 cm to petal flare.
Corolla tube color inside: RHS N155B (white) but more pure white, base color; RHS 144C (yellow-green) mid-veins; RHS 11A (yellow) and RHS 160B (greyed-yellow) secondary veins.
Corolla outside texture: Many glandular hairs of various sizes.
Floret form and number of petals: Funnel form, 5 lobed petals fused at base; Calyx 5 deeply lobed sepals.
Flower (limb) diameter: 3.8–4.0 cm.
Petal apex shape: Retuse.
Petal base shape: Fused.
Petal margin: Entire.
Waviness of petals: Weak.
Petal lobation: Moderate.
Petal texture: Papillose.
Sepals: 5.
Sepal color: RHS 137A (green).
Sepal length: 1.4–1.6 cm.
Sepal width: 0.35–0.40 cm.
Sepal shape: Oblong.
Sepal apex: Obtuse.
Sepal texture: Many glandular hairs of various sizes.
Lastingness of individual blooms: 4–8 days.
Fragrance: Slightly sweet.

THE REPRODUCTIVE ORGANS

Stamens: Five, 2 taller and 3 shorter.
Filament color: RHS 145D (yellow-green).
Pollen color: RHS 11C (yellow).
Pistil: One.
Stigma: RHS 145B (yellow-green).
Style color: RHS 145C (yellow-green).
Fruit seed set: Not observed.

DISEASE AND INSECT RESISTANCE

Not observed.

COMPARISON WITH KNOWN CULTIVARS

Compared to its female parent 99-296-3 as follows: The female parent has a light yellow flower, with lighter green leaves than 'Whip White'.

Compared to its male parent 99-264-4 as follows: The male parent has a flower color that is purple with a yellow throat.

I claim:

1. A new and distinct petunia plant as shown and described herein.

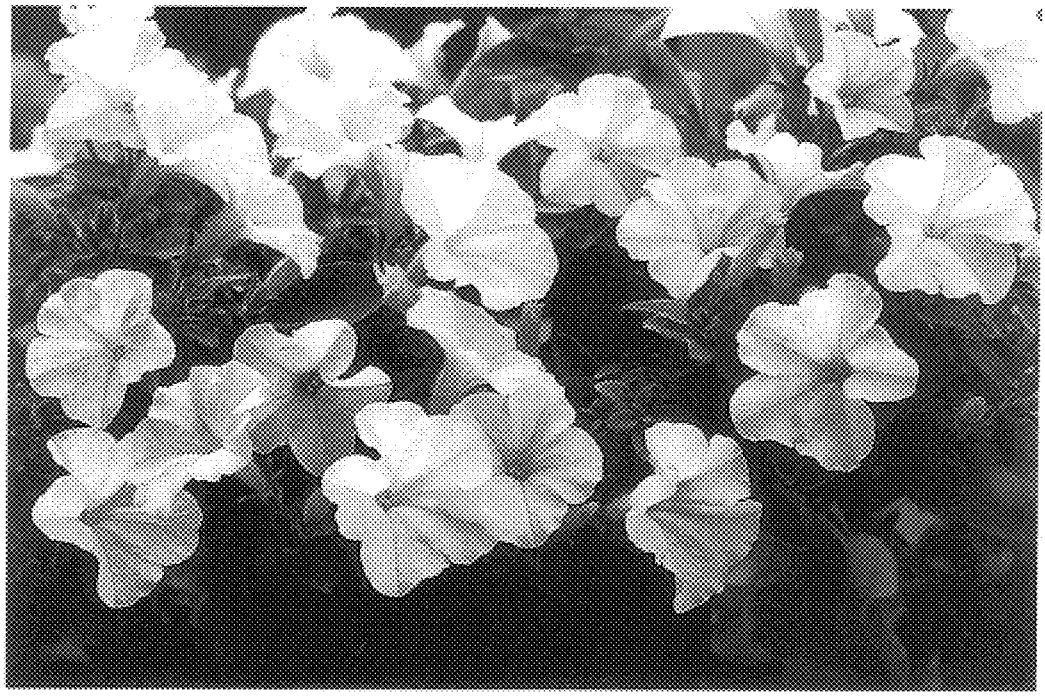

* * * * *